US008975077B2

(12) United States Patent
Aidun

(10) Patent No.: US 8,975,077 B2
(45) Date of Patent: *Mar. 10, 2015

(54) METHODS FOR DISPERSING SOMATIC PLANT EMBRYOS

(71) Applicant: Georgia Tech Research Corporation, Atlanta, GA (US)

(72) Inventor: Cyrus K. Aidun, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,125

(22) Filed: Feb. 6, 2013

(65) Prior Publication Data

US 2013/0153691 A1 Jun. 20, 2013

Related U.S. Application Data

(63) Continuation of application No. 12/937,240, filed as application No. PCT/US2009/039981 on Apr. 9, 2009, now Pat. No. 8,394,633.

(60) Provisional application No. 61/043,851, filed on Apr. 10, 2008.

(51) Int. Cl.
*C12N 5/02* (2006.01)
*A61B 17/43* (2006.01)
*A01H 4/00* (2006.01)
*C12N 5/04* (2006.01)

(52) U.S. Cl.
CPC . *A01H 4/001* (2013.01); *C12N 5/04* (2013.01)
USPC ............................................ 435/430; 600/33

(58) Field of Classification Search
USPC ........................................................ 435/430
See application file for complete search history.

(56) References Cited

U.S. PATENT DOCUMENTS

| | | | |
|---|---|---|---|
| 4,146,468 A | 3/1979 | Wilson | |
| 4,959,158 A | 9/1990 | Meikrantz | |
| 5,284,765 A | 2/1994 | Bryan et al. | |
| 5,563,061 A | 10/1996 | Gupta | |
| 5,591,340 A | 1/1997 | Meikrantz et al. | |
| 5,821,116 A | 10/1998 | Herman | |
| 6,193,647 B1 * | 2/2001 | Beebe et al. | 600/33 |
| 6,684,564 B1 | 2/2004 | Hirahara | |
| 7,568,309 B2 | 8/2009 | Hirahara | |
| 8,394,633 B2 * | 3/2013 | Aidun | 435/430 |
| 2005/0246802 A1 | 11/2005 | Attree et al. | |
| 2008/0108137 A1 * | 5/2008 | Rigaut | 435/383 |
| 2012/0202289 A1 | 8/2012 | Aidun | |

FOREIGN PATENT DOCUMENTS

| | | |
|---|---|---|
| CN | 101035426 A | 9/2007 |
| WO | 96/25484 A1 | 8/1996 |
| WO | 2009/029852 A2 | 3/2009 |
| WO | 2009/126757 A2 | 10/2009 |
| WO | 2009/126758 A1 | 10/2009 |
| WO | 2011/042888 A2 | 4/2011 |

OTHER PUBLICATIONS

Rodriguez et al. (Plant Cell, Mechanical purification of torpedo stage somatic embryos of *Daucus carota*. Tissue and Organ Culture 23:9-14, 1990).*
Office Action received for European Patent Application No. 09730557.7, mailed on Mar. 25, 2011, 3 pages.
Final Office Action received for U.S. Appl. No. 12/937,240, mailed on Aug. 27, 2012, 7 pages.
Non Final Office Action received for U.S. Appl. No. 12/937,240, mailed on Feb. 23, 2012, 6 pages.
Non Final Office Action received for U.S. Appl. No. 12/937,240, mailed on Jan. 9, 2012, 9 pages.
Notice of Allowance received for U.S. Appl. No. 12/937,240, mailed on Nov. 19, 2012, 7 pages.
Restriction Requirement received for U.S. Appl. No. 12/937,240, mailed on Nov. 11, 2011, 7 pages.
Office Action received for Chinese Patent Application No. 200980112745.4, issued on Dec. 29, 2011, 10 pages (6 pages of English Translation and 4 pages of Office Action).
Belmonte et al., "Alteration of the glutathione redox state improve apical meristem structure and somatic embryo quality in white spruce (*Picea glauca*)", Journal of Experimental Botany, vol. 56, No. 419, 2005, pp. 2355-2364.
International Preliminary Report on Patentability received for PCT Patent Application No. PCT/US2009/039981, completed on Mar. 22, 2010, 4 pages.
International Search Report received for PCT Patent Application No. PCT/US2009/039981, mailed on Sep. 3, 2009, 3 pages.
Written Opinion of the International Search Authority received for PCT Patent Application No. PCT/US2009/039981, mailed on Sep. 30, 2009, 4 pages.
Rodriguez et al., "Mechanical purification of torpedo stage somatic embryos of *Daucus carota* L.", Plant Cell, Tissue and Organ Culture, vol. 23, No. 1, 1990, pp. 9-14.

(Continued)

*Primary Examiner* — Annette Para
(74) *Attorney, Agent, or Firm* — Morrison & Foerster LLP

(57) ABSTRACT

Methods and devices for dispersion of clusters of somatic plant embryos suspended in a liquid are disclosed. The methods comprise i) subjecting the clusters of embryos to fluid dynamics forces causing axially extensional strain and radially compressional strain and ii) subjecting the clusters of embryos to fluid dynamics forces causing axially compressional strain and radially extensional strain fluid dynamics and iii) repeating said steps in sequence until the individual embryos are separated from each other. The devices may comprise a flow channel including at least one constriction, such that clusters of embryos flowing through the flow channel are first subjected to axially extensional strain and radially compressional strain, and then to axially compressional strain and radially extensional strain from fluid dynamics forces.

21 Claims, 4 Drawing Sheets

(56) References Cited

OTHER PUBLICATIONS

Office Action received for Chinese Patent Application No. 201080045536.5, mailed on Mar. 15, 2013, 22 pages (13 pages of English Translation and 9 pages of Office Action).
Office Action received for Chinese Patent Application No. 201080045552.4, mailed on Jul. 15, 2013, 15 pages (8 pages of English Translation and 7 pages of Office Action).
Extended European Search Report received for European Patent Application No. 10821666.4 mailed on Jun. 26, 2013, 6 pages.
European Search Report received for European Patent Application No. 10821666.4 mailed on Sep. 13, 2013, 8 pages.
International Preliminary Report on Patentability received for PCT Patent Application No. PCT/IB2010/054557, mailed on Apr. 19, 2012, 8 pages.
International Search Report and Written Opinion received for PCT Patent Application No. PCT/IB2010/054557, mailed on Apr. 22, 2011, 10 pages.
International Preliminary Report on Patentability received for PCT Patent Application No. PCT/SE2010/051083, mailed on Apr. 19, 2012, 10 pages.
International Search Report and Written Opinion received for PCT Patent Application No. PCT/SE2010/051083, mailed on Nov. 9, 2010, 12 pages.
Office Action received for New Zealand Patent Application No. 599717, mailed on Dec. 4, 2012, 1 page.
Restriction Requirement received for for U.S. Appl. No. 13/500,904 mailed on Oct. 21, 2013, 5 pages.
Restriction Requirement received for for U.S. Appl. No. 13/500,904 mailed on Jan. 29, 2014, 5 pages.
Greenspan et al., "On the Centrifugal Separation of a Bulk Mixture", International Journal of Multiphase Flow, vol. 11, No. 6, 1985, pp. 825-835.
Harrell et al., "Machine Vision Based Analysis and Harvest of Somatic Embryos", Computers and Electronics in Agriculture, vol. 9, 1993, pp. 13-23.
Parsheh et al., "Variation of Fiber Orientation in Turbulent Flow Inside a Planar Contraction with Different Shapes", International Journal of Multiphase Flow, vol. 32, 2006, pp. 1354-1369.
Von Arnold et al., "Spruce Embryogenesis", Methods in Molecular Biology, vol. 427, 2008, pp. 31-47.
Examination Report received for New Zealand Patent Application No. 599717, mailed on Feb. 28, 2014, 2 pages.
Non-Final Office Action received for U.S. Appl. No. 13/500,904, mailed on Jun. 5, 2014, 8 pages.
Non-Final Office Action received for U.S. Appl. No. 13/500,886, mailed on May 22, 2014, 6 pages.

\* cited by examiner

METHODS FOR DISPERSING SOMATIC PLANT EMBRYOS

CROSS-REFERENCE TO RELATED APPLICATIONS

The present application is a continuation of U.S. application Ser. No. 12/937,240, filed Oct. 8, 2010, which is a U.S. National Phase patent application of PCT/US2009/039981, filed Apr. 9, 2009, which claims priority to U.S. Provisional patent application Ser. No. 61/043,851, filed Apr. 10, 2008, all of which are hereby incorporated by reference in the present disclosure in their entirety.

This invention was made based on a joint research agreement between Georgia Tech Research Corporation and Swe-Tree Technologies AB.

BACKGROUND TO THE INVENTION

General Introduction to Problem Area

Somatic embryogenesis in plants is a process in which somatic embryos are formed from an initial explant being a cell in a plant tissue. The somatic embryos formed are genetically identical copies of the plant providing the initial explant. The process of somatic embryogenesis thereby offers a tool to obtain large numbers of genotypically identical plants for multiplication of selected genotypes of commercial interest, for conservation of endangered species or for generating genetically uniform plant material for research purposes.

Physiological Background to the Procedures Related to the Problem

To produce plants from somatic embryos of conifers, a multi-step procedure is applied to meet the physiological needs of the different stages of development as described below and shown in FIG. 1. Initiation of somatic embryogenesis starts with induction of somatic embryos from an initial explant, typically an immature zygotic embryo, on a solidified culture medium containing plant growth regulator. Somatic embryos continue to form, typically on the same composition culture medium, and a proliferating embryogenic culture form. At the proliferating stage, several of the key features generally regarded as beneficial for the process of somatic embryogenesis process, take place: (i) the mass propagation of genotypically identical propagules through unlimited multiplication of immature somatic embryos; (ii) cryogenic storage of proliferating embryos substantiates an virtually eternal store of clones, i.e. a clone bank is established, (iii) transgenic modification of the immature somatic embryo allow for large scale propagation of genetically improved propagules. At the next step in the procedure, the proliferating somatic embryo is subjected to a growth medium that triggers embryo development to progress into the maturation stage. Conversion from proliferation to maturation only occurs in a fraction of the proliferating embryos in the culture. Low conversion rates are encountered more frequently in genotypes from recalcitrant conifer species, but are common in all conifer species as well as other plant species. The manual labour needed to collect embryos increase with the decrease in conversion rate, and thereby the cost and risk of contamination and other inaccuracies. Low conversion rate from proliferation to maturation is a major bottleneck for commercial large scale applications of somatic embryogenesis procedures. For germination, mature somatic embryos are subjected to different culture regimes to induce root- and shoot formation, in as number of different steps; desiccation, sucrose treatment, red tight, induction, and blue light stimulation. Thereafter, germinated embryos deemed appropriately developed are transferred to a compost material and gradually transferred to an environment ex vitro during winch the sucrose content is reduced. The different treatments during germination into a plant requires repeated manual handling of individual germinants and plants adding a considerable cost to the overall procedure.

Production of Plants from Somatic Embryos

The prior art procedure for producing plants from somatic embryos requires manual handling at several steps making the procedure time consuming, expensive and inaccurate.

For conifer species, standard procedures used involve several steps when manual handling is required. The general procedure is outlined in FIG. 1 (sec e.g. von Arnold S. Clapham D, Spruce embryogenesis. 2008. *Methods Mol Biol*. 2008; 427:31-47; Belmonte M F, Donald G. Reid D M. Yeung E C and Stasolla C. 2005. Alterations of the glutathione redox state improve apical mainstem structure and somatic embryo quality in white spruce (*Picea glauca*), *J Exp Biol*, Vol. 56, No. 419, pp, 2355-2364).

There are four steps that rely on manual handling to obtain a small plant from the mature somatic embryo as seen in FIG. 1. The first manual interaction is when [1] the mature embryo is isolated from immature embryos (120), and placed horizontally in a plastic container under sterile conditions; the second [2] occur after 3-7 days of resting (130), then mature embryo is transferred to a gelled culture medium for initiation of germination processes. The germinated somatic embryo will under appropriate culture medium composition and light conditions initiate roots (140). The third manual transfer [3] is when the germinant having a small root formed is transferred to an upright position with the root partially immersed in liquid germination media (150). The fourth [4] and final transfer is when the germinated embryos has a to root and small lateral roots, then it is transferred into a solid substrate in a pot for further plant formation (160).

TABLE 1

List of designations pertaining to FIG. 1.

| Item | Designation |
|---|---|
| 100 | Mature embryo |
| 101 | Crown of a mature embryo |
| 102 | Foot of a mature embryo |
| 103 | Width of crown of a mature embryo |
| 104 | Length of a mature embryo |
| 120 | Maturation phase |
| 130 | Resting phase |
| 140 | Germination phase |
| 150 | In vitro plant formation phase |
| 160 | Ex vitro plantformation phase |

Conversion from proliferation to maturation only occurs in a fraction of the proliferating embryos in the culture. Low conversion rates are encountered more frequently in genotypes from recalcitrant conifer species, but are common in all conifer species as well as other plant species. The manual labour needed to collect embryos increase with the decrease in conversion rate, and thereby the cost and risk of contamination and other inaccuracies. Low conversion rate from proliferation to maturation is a major bottleneck for commercial large scale applications of somatic embryogenesis procedures. For germination, mature somatic embryos are subjected to different culture regimes to induce root- and shoot formation, in a number of different steps; desiccation, sucrose treatment red light induction, and blue light stimulation. Thereafter germinated embryos deemed appropriately developed arc transferred to a compost material and gradually transferred to an environment ex vitro during which the sucrose content is reduced. The different treatments during Remittal into a plant requires repeated manual handling of individual germinants and plants adding a considerable cost to the overall procedure.

In the hitherto available method for producing plants from somatic embryos the embryos are picked out manually from the immature embryogenic tissue is time-consuming and ineffective. It would therefore be desirable to provide a way to make the separation of the embryos more effective. The somatic embryos produced are daily glued together by immature embryogenic tissue into clusters. It is an object of the invention to provide effective means of producing somatic plant embryos, an automated means for gently dispersing the clusters of somatic embryos into individual embryos detached from the embryogenic tissue. The invention relates to a method and a device for such dispersion.

SUMMARY OF THE INVENTION

The present invention relates to methods and devices for gently dispersing clusters somatic plant embryos into individual embryos and it an embryogenic tissue.

A method of dispersion of clusters of plant embryos suspended in a liquid into individual plant embryos is disclosed, said method including at least one dispersion sequence, comprises the following steps:
 i) subjecting the clusters of embryos to fluid dynamics forces causing extensional strain and radially compressional strain;
 ii) subjecting the clusters of embryos to fluid dynamics forces causing compressional strain and radially extensional strain from fluid dynamics forces:
 repeating said step, in sequence until individual embryos are separated from each other.

Preferably, the strength of the extensional d compressional strains increases each repeated sequence.

A disperser for separating individual embryos contained in clusters of embryos is disclosed, comprising a flow channel including at least one constriction such that clusters of embryos flowing through the flow channel are first subjected to axially extensional strain and radially compressional strain, and then to axially compressional strain and radially extensional strain from fluid dynamics forces.

Preferably, the flow channel comprises at least two constrictions, each constriction having an inner diameter, which is equal to or smaller than the inner diameter of the constriction immediately up-stream of thereof.

Preferably, the flow channel includes an intermediate portion having, a constant cross-section, between each constriction.

Preferably, each intermediate portion has an inner diameter, which is equal to or smaller than the inner diameter of the intermediate portion immediately up-stream of thereof Preferably, each intermediate portion may have a length at least equal to the clusters of embryos to be dispersed. Preferably, the length of each intermediate portion is in the interval from 2.5 mm to 60 mm, more preferably from about 5 mm to about 30 mm. The number of constrictions may be 3-100, preferably 5-20, most preferably about 10. Preferably, the constrictions have a cross-sectional area m the interval from 0.75 to 1300 mm$^2$, more preferably in the interval from 3 to 32 mm$^2$.

The flow channel may have axisymmetric cross-section. The flow channel may have an essentially circular or oval cross-section.

At least part of the flow channel may have a non-axisymmetric cross-section such as a rectangular cross-section. The cross-section of each non-axisymmetric constriction, having a maximal dimension, may preferably be oriented such that the maximal dimension of each constriction is rotated, preferably at least 30°, more preferably about 90° in relation to maximal dimension of the next non-axisymmetrie constriction in sequence. The cross-section of each constriction may represent a rectangle, having a first and a second side, wherein the first side is longer than the second side, and the constrictions are oriented such that first side of each constriction is perpendicular to the first side of the next constriction in sequence having a rectangular cross-section.

The advantages of the method and the device of dispersion include;
 (1) Not requiring moving parts, and therefore being robust
 (2) Being naturally applicable to a continuous flow system thereby not requiring operation in hatch mode
 (3) Being gentle to the embryos
 (4) Being fast; the dispersion using the device requires only a few seconds to disperse hundreds of embryos
 (5) The device being compact and completely end used allows easy sterilization.

Definitions

The terms somatic embryo, somatic plant embryo and plant somatic embryo are used interchangeably. The terms refer to plant embryos derived from somatic tissue of a plant.

*Norway spruce* is a spruce species with the Latin name *Picea abies* native to Europe.

The terms fluid dynamics and hydrodynamics are used interchangeably and refer to the same physical principles of flow of fluids.

The terms channel and rube are used interchangeably without specific implication to the geometry of the passage unless otherwise stated.

The orthogonal directions in polar coordinates are given by axial, radial and angular (azimuthal) directions. These directions correspond to the central axis of a cylinder which is normal to the circular cross-section of the cylinder, and the radial and angular directions pointing along the radius and normal to the radius on the cross-sectional surface, respectively.

Axisymmetric flow refers to flow inside a tube where the cross-sectional surface of the tube is always circular and therefore, there is symmetry with respect to the axis of the tube. In other words, nothing changes along the angular (or azimuthal) direction.

Stress is force per unit area.

Strain is the geometrical measure of deformation representing the relative displacement between points in the material body; it is represented as the ratio or percentage of deformation in relation to the original dimension.

Normal strain defines the ratio or percentage amount of stretch or compression along material line elements (ratio of the deformation to the original length in the direction of the deformation).

Shear strain defines the ratio or percentage amount of deformation relative to the original dimension associated with the sliding of material plane layers over each other.

Extensional strain is a normal strain where the element stretches.

Axially extensional strain is an element that stretches along the axial direction.

Radially extensional strain is an element that stretches along the radial direction.

Compressional strain is a normal strain where the element contracts.

Axially compressional strain refers to deformation of an element that contracts along, the axial direction, Radially compressional strain refers to deformation of an element that contracts along the radial direction.

Rate of Stain is the change in strain with respect to time

Hydraulic diameter, $D_h$, is a term used to characterize flow in noncircular tubes and channels. By definition, it is given by $D_h = 4 A/S$ where A is the cross-sectional area of the noncircular tube or channel and S is the wetted perimeter of the cross-section, Mean velocity in a channel is defined as the volumetric flow rate divided, by the cross-sectional area of the channel.

Contraction ratio is defined as the ratio of the mean velocity at the outlet to the mean velocity at the inlet in a channel.

Mean stress is the stress that is averaged over a surface.

Mean rate of strain is the rate of strain averaged over a surface.

Dynamic viscosity of a fluid is the ratio of shear stress to rate of shear strain in a Newtonian fluid element. Water, glycerin, silicone oil are examples of Newtonian fluids.

Rate of strain profile is a profile showing the variation of the rate of strain.

Unit of length in millimeter is abbreviated as "mm".

Unit of rate of strain as reciprocal second is abbreviated as "1/s".

In general, a flow with higher average rate of strain will impose higher average stress on a particle (or embryo) or on a cluster of particles (or cluster of embryos) suspended in the fluid.

DETAILED DESCRIPTION OF THE INVENTION

Method of Dispersing Somatic Embryos

Figure 1:
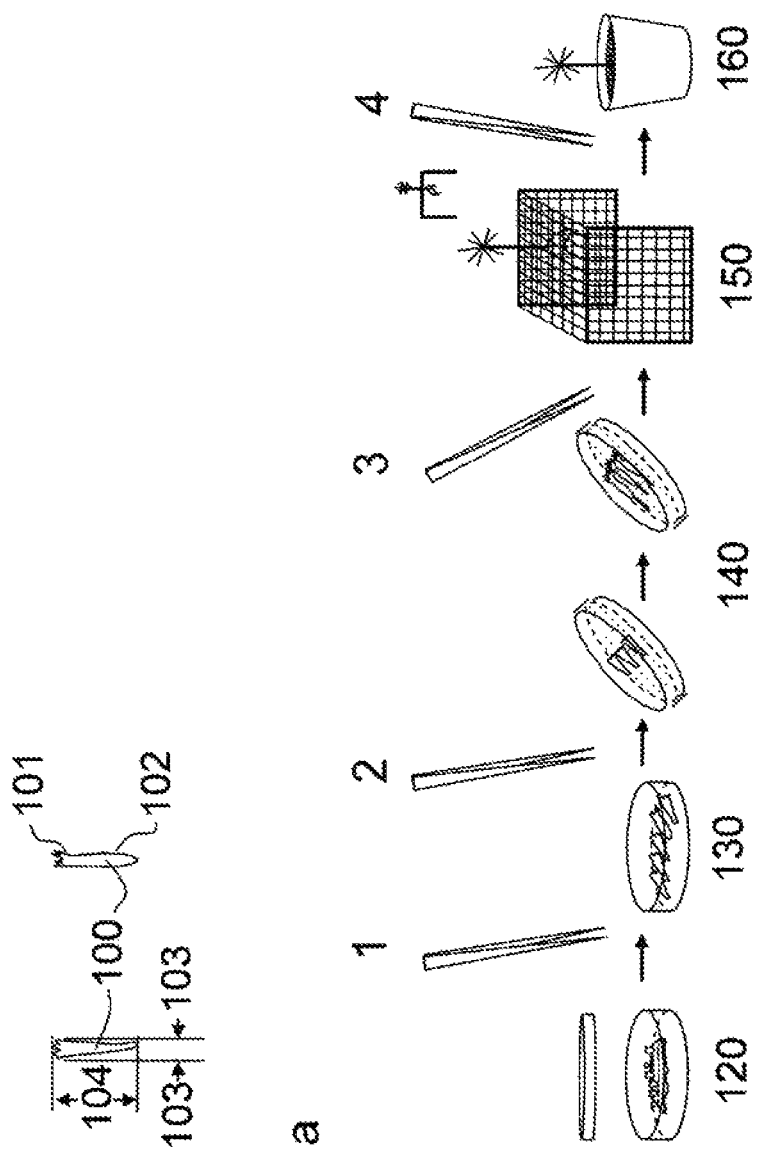
FIG. 1 illustrates a general process of producing somatic plant embryos.

A method of dispersion of clusters of plant embryos suspended in a liquid into individual plant embryos is provided. Said method includes at least one dispersion sequence, which comprises the following steps:
 i) subjecting the clusters of embryos to fluid dynamics forces causing axially extensional strain and radially compressional strain
 ii) subletting the clusters of embryos to fluid dynamics forces causing axially compressional strain and radially extensional strain from fluid dynamics forces.

Said steps are repeated in sequence until the individual embryos are separated from each other. The strength of the extensional and compressional strains may be increased with each repeated sequence.

Device for Dispersing Somatic Embroys

To illustrate the construction of the disperser device, certain possible embodiments are disclosed in detail. The level of detail should not be construed as limiting unless explicitly stated so.

Overall Construction

A disperser device for separating individual embryos contained in clusters of embryos is provided. The devices disclosed are for use with clusters of somatic embryos held together by immature embryogenic tissue suspended in a liquid flowing though the device. The liquid may be any liquid which is not too viscous to flow in the apparatus, and which is benign to the embryos, preferably water.

The disperser device comprises a flow channel. The flow channel may be manufactured as a single entity or as two or more parts comprising an individual segment each. The flow channel may for example be constructed of two parts, first segment (1)/(81) and second segment (2)/(82), see FIGS. 3/4, respectively. It may he advantageous to manufacture the device with several individual segments as this will enable the device to be more easily adapted to different starting materials and will simplify cleaning and maintenance. For example, the disperser flow channel segments (1) and (2) may be connected to a source of flowing fluid comprising clusters of embryos by a tube (41) at the inlet (1). The firm segment (1) of the disperser flow channel may be connected to the second segment (2) by a connecting tube (41*a*). In this example, the dispersed embryos leave the second segment (2) at the outlet (O) connected to an outlet tube (90).

The disperser device flow channel comprises at least one constriction, such that clusters of embryos flowing through the flow channel are first subjected to axially extensional strain and radially compressional strain, and then to axially compressional strain and radially extensional strain from fluid dynamics forces. When the flow channel comprises at least two constrictions, each constriction may have an inner diameter, which is equal to or smaller than the inner diameter of the constriction immediately up-stream of thereof in order to apply effective dispersing forces to the clusters of embryos. Preferably, the disperser device has a set of constrictions. The number of constrictions in a set of constrictions may for example vary from 1 to 100, 1 to 20. from 4 to 16 or 6 to 12, and the preferred number of constrictions is about 10, and depends on the nature of the clusters to be dispersed. Higher number provides more vigorous dispersing but increases the stress on the embryos to be dispersed.

The now channel may comprise an intermediate portion having an essentially constant cross-section, between each constriction. Each intermediate portion can have an inner diameter, which is equal to or smaller than the inner diameter of the intermediate portion immediately up-stream of thereof, thereby increasing the dispersing forces step by step.

Preferably, the flow channels have an essentially circular cross-section, except for the constrictions which are subject to special considerations, as described below. Other geometries (such as oval, hexagonal, octagonal, rectangular with rounded corners, or triangular with rounded corners) may be used as long as the embryos do not become damaged during their passage of the flow channels as result of the geometry. Tubes having circular cross-sections are easy to manufacture. Also preferably, the flow channels are smooth on the inside. Any roughness on the inner surfaces may easily damage the delicate embryos and is thus best avoided.

Fluid Dynamics Considerations

It is critical to avoid imposing too much hydrodynamic stress which could cause damage to the embryos. On the other hand, the stresses must be sufficient to disperse at least a significant fraction of the clusters. The optimal levels of stresses for the clusters of embryos of a particular type, cell line or species to be dispersed may need to be determined experimentally. Once the optimal levels have been determined or obtained, the necessary disperser device parameters may be calculated accordingly. Alternatively, a disperser having minimum and maximum dimensions dictated by the embryo size and cluster size, exerting gentle stress may be constructed to determine whether such dispersion is efficient for the embryos at hand (see below for details). If not, a disperser with more rigorous dispersing activity may be constructed and tested, and the process repeated until a satisfactory result is obtained.

Certain constants are preferably decided upon before calculating the remaining parameters of the disperser design. Dynamic viscosity of the fluid affect the hydrodynamic forces and the intended fluid should, be chosen. Preferably, the fluid is essentially water., having well-known dynamic viscosity which can be taken as a constant in a constant temperature environment for the design of a disperser device. The dynamic viscosity of water is not generally significantly affected by small amounts of salts, simple carbohydrates, amino-acids or similar low molecular weight compounds. If the dynamic viscosity of the fluid cannot be obtained from literature, it may he experimentally measured by means known to the skilled person.

Flow rate also affects the hydrodynamic forces. The desired flow rate may in part depend on desired capacity of the disperser device, wherein faster flow may allow higher capacity. For simplicity, the design of the disperser is preferably based on a constant flow rate, which can be taken as another constant for the design of a disperser device. By varying the flow rate, the hydrodynamic forces may then be fine-tuned without having to modify the dimensions of the device.

According to the invention, the inner dimensions of the flow channels vary along the flow direction forming at least one constriction, preferably a set of constrictions. The inner dimensions at these constrictions are a critical parameter, since it is the value of the inner dimensions at the constriction that dictate the magnitude of the extensional and compressive hydrodynamic strains, and it is the said extensional and compressive hydrodynamic strains that impose extensional and compressive stresses on the clusters of embryos, gently forcing the embryos to separate from each other.

According to the invention, the dimensions of the constrictions are selected according to the level, of extensional and compressive stress that is required to he imposed on the cluster of embryos and the size of the cluster and the specific species of embryo to be dispersed, taking into account the previously chosen fluid type and flow rate. Preferably, the inner dimensions of the constrictions decrease sequentially from the largest dimensions at the upstream inlet side of the tube to the smallest diameter at the downstream outlet of the tube. The smallest inner dimensions at the extreme downstream side (at the outlet where the embryos have been fully dispersed) have to be at least large enough to allow a single embryo to pass without damaging the embryo. A preferred minimum dimension is equal or larger than the broadest part of an embryo to be dispersed.

Key Dimensions

Considering the above, several key dimensions need to be considered for the flow channels:
  I. Inner cross-section dimensions and geometry of constrictions
  II. Length of constrictions
  III. Inner cross-section dimensions and geometry outside of constrictions
  IV. Length of sections outside or between the constrictions The minimum cross-sectional dimension of the flow channel should be larger than the largest dimension of the largest embryo to be dispersed. The maximum cross-sectional dimension of the flow channel does not have to be larger than the largest dimension of the largest cluster to be dispersed. The intermediate portion (inter-constriction) dimensions of the flow channel do not have to be larger than the largest dimension of the largest cluster to be dispersed.

Figure 2:
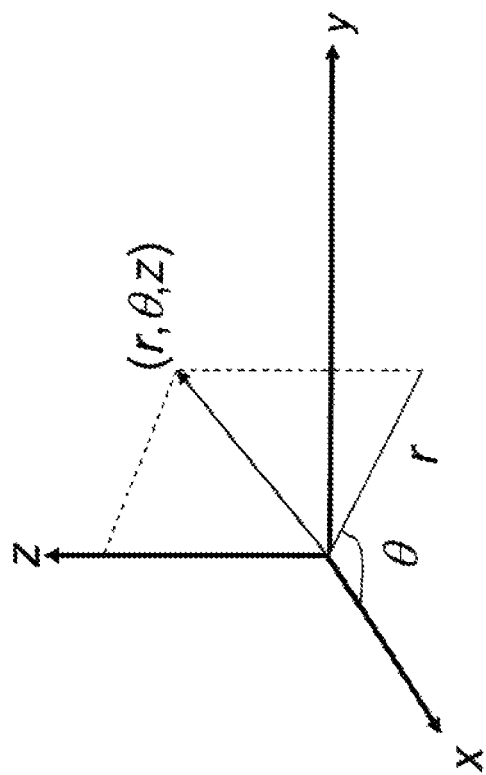
FIG. 2, illustrates the coordinate parameters used in the description.

For illustrative purposes, a cylindrical coordinate system is defined, as illustrated in FIG. 2. The general direction of the flow in a disperser device is in the axial direction designated by axis z. The flow also has radial component of velocity in the direction r as it expands and contracts through the disperser device. The axial, radial and angular (in the direction of θ) components of the fluid velocity are defined as $u_z$, $u_r$, and $u_\theta$, respectively.

The term axisymmetric flow is defined to mean that nothing changes in the angular direction, or more precisely $$\frac{\partial(\bullet)}{\partial \theta} = 0$$

where (●) represents any flow variable. The term $$\frac{\partial}{\partial \theta}$$

is the usual symbol used in mathematics to mean partial derivative which measures the rate of change of a dependent variable with respect to the independent variable in the denominator keeping all other independent variables constant. In an axisymmetric embodiment of the disperser device, the flow is axisymmetric and the angular velocity component $u_\theta$ is zero.

The rate of axial strain in flow at the centreline of an axisymmetric tube is defined by $$\frac{\partial u_z}{\partial z},$$

where when this quantity is positive the flow is in extensional strain and when negative flow is in compressional strain. Similarly, the rate of radial strain is measured by $$\frac{\partial u_r}{\partial r}$$

where in general when positive represents radial extension and when negative represents radial compression.

Following the same definition as above for axisymmetric extension and compression, for a non-axisymmetric disperser device, the flow is not axisymmetric, and thereby all components of the rate of strain tensor will be nonzero.

Determining lengths of constrictions and intermediate portions

The length of different parts of the disperser can be calculated based on various axial profiles for the mean rate of strain, $$\frac{dU}{dz},$$

variation, where U is the symbol for the mean velocity defined as the volumetric flow rate divided by the cross-sectional area of the tube in the r-θ plane. The rate of strain along the flow direction can be constant, vary linearly with z, vary quadratically with z, vary as the rate of strain varies along a channel with 'flat walls', or have other functional dependence on z.

The precise functional dependence and variation of the mean rate of strain on z is not as significant as the actual magnitude of the the mean rate of strain. For simplicity, we use the case when the mean rate of strain, B, defined by $$B = \frac{dU}{dz},$$

is a constant. Thus, the length of each section (such as for example i=61, . . . 80 in FIG. 4), symbolized by $L_i$ for the axisymmetric tube can be computed based on the constant mean rate of strain in that section, $B_i$, given by $$L_i = \frac{Q}{\pi B_i} \left[ \frac{1}{R_{1,i}^2} - \frac{1}{R_{0,i}^2} \right] \quad \text{Equation 1}$$

where Q is the volumetric flow rate which is always constant along the channel (based on the principle of conservation of mass), R is the radius of the tube, and the subscripts "0" and "1" associated with the radius R define the inlet and outlet radius of each section. respectively. This relation for length from now on is referred to as Eq. (1). The mean rate of strain $B_i$ can be positive or negative, which means that the embryo cluster experiences a mean rate of extensional strain for position $B_i$ and a mean rate of compressional strain for negative value of B. A large number of combinations for the length $L_i$ and the mean rate of strain $B_i$ are possible.

Eq. (1) can be generalized to the non-axisymmetric case by using the concept of the hydraulic radius, $R_h$, for each case, which is defined as one half the hydraulic diameter, or mathematically stated $R_h \equiv D_h/2$ where $D_h$ is the hydraulic diameter as defined above.

The equations to determine the length of the contraction or expansion section based on linear, quadratic or fiat wall formulation can also be considered. Such equations can be found in the literature for various types of contractions (for reference, see e,g., Parsheh M., Brown, M., and Aidun, C. K., "Fiber Orientation in a Planar Contraction: Shape Effect" *Int. J. Multiphase Flow,* 32, 1354-1369, 2006.)

The case of linear or quadratic mean rate of strain can be considered if there are limitations for the length of the disperser unit. However, the constant mean rate of strain will be sufficient to disperse the cluster if applied in gradually increasing magnitude of the mean rate of strain.

The length of intermediate: portions (inter-constriction parts) of the flow channel is determined based on the size of the embryo cluster to he dispersed and should be at least equal to the largest dimension of any cluster to he dispersed. For example, in the case of Norway spruce cluster matured in laboratory Petri dish, the section of the straight tube needs to be at least 10 mm ion since the cluster is about 10 mm in size. For embryo clusters matured in a bioreactor where the size of the cluster is larger, the tube length and the initial diameter should be adjusted to accommodate the larger size of the cluster. As the clusters become smaller as the dispersion progresses the length of the intermediate portions may also successively decrease. For instance, the length of the intermediate portions may be about 60 mm (preferably about 30 mm) in the beginning of the disperser flow channel and about 2.5 mm (preferably about 5 mm) at the end of the flow channel.

Determining Cross-section Dimensions

The mean hydrodynamic stress is proportional to the mean rate of strain through the dynamic viscosity of the fluid, which is preferably water.

The contraction ratio, $CR_i$, is defined as the ratio of the inlet to outlet cross-sectional area or mean velocity, or written in terms of the hydraulic radius, this can be stated as, $$CR_i \equiv \frac{R_{o,i}^2}{R_{1,i}^2}, \quad \text{Equation 2,}$$

since area is proportional to radius squared. This relation from now on is referred to as Eq. (2). Examples of these parameters computed for several cases are shown in Table 5. For Norway spruce, the contraction ratio of 3 corresponding to a mean rate of strain, B of 11 reciprocal second (1/s) for contraction diameter from 9.5 millimeter (mm) to 5.5 mm which is considered to exert gentle extensional and compressional stress on the embryo cluster. Where the contraction ratio of 7 corresponding to a mean rate of strain of 36 (1/s) for contraction diameter from 9.5 mm to 3.5 mm is considered to be a relatively strong extensional and compressional stress. Whenever the flow encounters a converging passage or otherwise referred to as a contraction characterized by the cross-sectional area of the passage decreasing in the flow direction, the flow in general will experience an axial extensional rate of strain and a radial compressional rate of strain. The opposite condition is when the flow encounters a diverging passage or otherwise referred to as a expansion characterized by the cross-sectional area of the passage increasing in the flow direction, the flow in general will experience an axial compressional rate of strain and a radial extensional rate of strain. The terms "axial" and "radial" refer to the spatial directions along the center axis of the tube in general direction of the flow (axial), and along the radius of the tube from center toward the surface of the tube normal to the axial direction (radial). When the cluster enters a contraction, it is elongated in the flow direction. As the cluster leaves a contraction and enters the expansion, it is compressed along the flow and stretched along the radial direction. This repeated elongation and compression through the disperser imposes gentle force on the individual embryos relative to each other. For example, when two attached embryos in a cluster are entering a contraction, the leading embryo is forced to move faster than the trailing embryo because the fluid surrounding the leading embryo is moving faster downstream than the fluid surrounding the trailing embryo. This action results in a gentle and yet finite pull imposed on one embryo relative to the other encouraging the embryos to separate. On the other hand, when the pair of embryos is entering an expansion, the embryos are pressed toward each other along the axial direction but pulled away from each other in the radial direction further encouraging the embryos to separate.

Axisymmetric Cross-sections

The flow channel may have essentially axisymmetric cross-section throughout the length. For example, the flow channel may have an essentially circular cross-section.

Non-axisymmetric Cross-sections

At least part of the flow channel may have a non-axisymmetric cross-section. A non-axisymmetric disperser device (see e.g. FIG. 4), has a similar interior as the symmetric disperser device with the difference that the interior at the constrictions are not essentially circular.

The interior can be of any non circular cross section form, like oval, hexagonal, octagonal, triangular, elliptical, oval, square or rectangular in cross sections (43a), (45a), (47a), (49a), (53a), (55a), (57a), or (59a). Even irregularly shaped cross-sections may be used.

Axisymmetric cross-sections and non-axisymmetric cross-sections can be combined in the same disperser.

Preferably, the cross-section of each non-axisymmetric constriction, having a maximal dimension, is oriented such that the maximal dimension of each constriction is rotated, preferably at least 30° C., more preferably about 90 in relation to maximal dimension of the next non-axisymmetric constriction in sequence. Such differentially oriented cross-sections provide more effective dispersing than similarly oriented cross-sections.

Preferably, at least part of the flow channel has a rectangular cross-section. A preferred form of constrictions is a rectangular form with rounded corners.

Preferably, the cross-section of each constriction represents a rectangle, having a first and a second side, wherein the first side is longer and the second side, and the constrictions are oriented such that first side of each constriction is perpendicular to the first side of the next constriction in sequence having a rectangular cross-section. Such rectangular alternating cross-sections provide more effective dispersing than constant cross-sections.

The corners of the cross-sections are preferably rounded to minimize stresses to the embryos.

One way of expressing the size of the cross-sections is their cross-sectional area (perpendicular to the flow direction). The constrictions may have a cross-sectional area in the interval from 0.75 to 1300 mm$^2$, preferably in the interval from 3 to 32 mm$^2$.

Certain Specific Embodiments

Exemplary dimensions for an axisymmetric disperser are presented in Tables 2 and 3. The tables 2 and 3 give a preferred combination of dimensions for Norway spruce embryo clusters that are matured in a typical laboratory protocol or with a partially immersed bioreactor.

Exemplary dimensions for a non-axisymmetric disperser suitable for Norway spruce embryos are presented in Tables 4 and 5. In table 4, two alternative embodiments are presented designated Alt 1 and Alt 2. The constrictions are essentially rectangular and oriented in an alternating fashion. The disperser in Alt 1 imposes a more gradual extensional and compressive stress on the cluster of embryos where Alt 2 imposes a larger extensional and compressive stress. Alt 1 and Alt 2 are used depending on the maturation process of the embryos. When the embryo cluster is developed such that the cluster is loosely packed, Alt 1 in combination with the axisymmetric disperser would be sufficient to disperse the embryos. Otherwise, Alt 2 needs to be used.

Table 5 provides an example of the calculation based on Eq. (1), where the length of each fixed contraction is determined based on a fixed desired rate of strain or the rate of strain is calculated based on a fixed length, $L_j$. The first column in this table is the inlet hydraulic diameter, the second column is the outlet or the contraction hydraulic diameter. The third column is the contraction ratio calculated from Eq. (2). The fourth column is the volumetric flow rate with a typical value of 4000 mm$^3$/s which is equal to 4 milliliter/s.

The fifth column is the desired rate of strain of 10 (1/s). The sixth column is the calculated length of the contraction based on the fixed rate of strain in the fifth column, in this case 10 (1/s). The seventh column is the computed mean rate of strain based on the equal length of 10 mm from the following relation derived from Eq. (1)

$$B_i = \frac{Q}{\pi L_i}\left[\frac{1}{R_{1,i}^2} - \frac{1}{R_{0,i}^2}\right]. \quad \text{Equation 3}$$

This relation derived from Eq. (1) will be referred to as Eq. (3) from now on. For example, i=61, ... 80 for a device of FIG. 4.

EXAMPLES

Example 1

Preferred Dimensions of the Disperser

TABLE 2

Inner diameter measures of the flow channel

Figure 3:
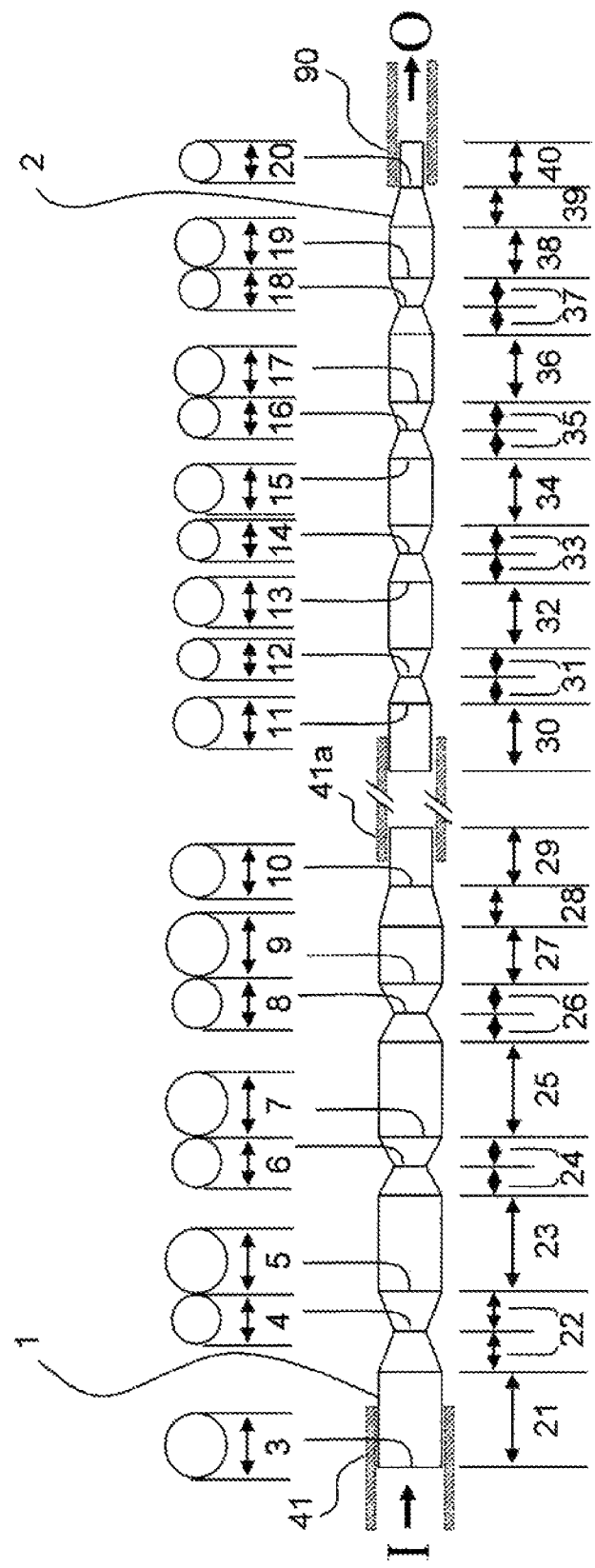
FIG. 3 illustrates details of as device of the invention where the flow channel is axisymmetric.

| Cross section position with reference to FIG. 3. | Inner diameter [mm] | Preferred Inner diameter for Norway Spruce (see example 2) |
|---|---|---|
| (3) | 3.0-10.0 | 9.0-9.5 |
| (4) | 2.0-9.0 | 5.0-5.5 |
| (5) | 3.0-10.0 | 9.0-9.5 |
| (6) | 2.0-9.0 | 4.75-5.0 |
| (7) | 3.0-10.0 | 9.0-9.5 |
| (8) | 2.0-9.0 | 4.0-4.25 |
| (9) | 3.0-10.0 | 9.0-9.5 |
| (10) | 2.0-9.0 | 5.5-6.0 |
| (11) | 2.0-9.0 | 5.75-6.0 |
| (12) | 1.0-8.0 | 3.25-3.5 |
| (13) | 2.0-9.0 | 5.75-6.0 |
| (14) | 1.0-8.0 | 3.0-3.25 |
| (15) | 2.0-9.0 | 5.75-6.0 |
| (16) | 1.0-8.0 | 2.5-2.75 |
| (17) | 2.0-9.0 | 5.75-6.0 |
| (18) | 1.0-8.0 | 2.5-2.75 |
| (19) | 2.0-9.0 | 5.75-6.0 |
| (20) | 2.0-9.0 | 5.75-6.0 |

TABLE 3

Exemplified preferred lengths for Norway Spruce of the different parts of an axisymmetric flow channel.

| Length on details in FIG. 3. | Length [mm] |
|---|---|
| (21) | 30.0 |
| (22) | 10.0 |
| (23) | 30.0 |
| (24) | 5.0 |
| (25) | 30.0 |
| (26) | 5.0 |
| (27) | 20.0 |
| (28) | 10.0 |
| (29) | 20.0 |
| (30) | 30.0 |
| (31) | 5.0 |
| (32) | 30.0 |
| (33) | 5.0 |
| (34) | 30.0 |
| (35) | 5.0 |
| (36) | 30.0 |
| (37) | 5.0 |
| (38) | 20.0 |
| (39) | 10.0 |
| (40) | 10.0 |

TABLE 4

Figure 4:
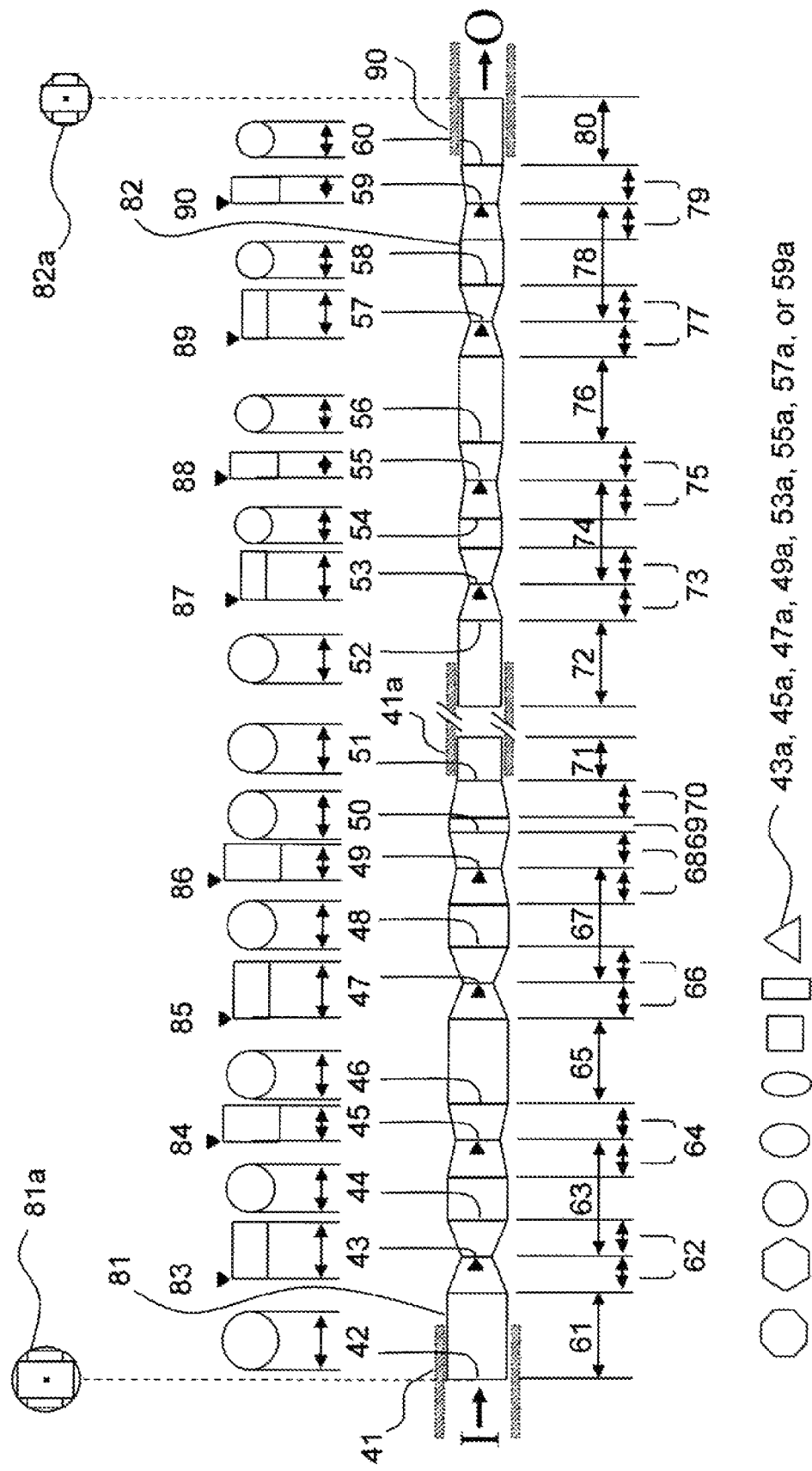
FIG. 4 illustrates details of devices of the invention where parts of the flow channel are non-axisymmetric.

Exemplified inner cross-section dimensions for Norway spruce, with reference to FIG. 4.

| Shape of inner section | Inner dimensions [mm] | | Black arrow side [mm] (83)-(90) | | Width side [mm] | |
|---|---|---|---|---|---|---|
| | Alt. 1 | Alt. 2 | Alt. 1 | Alt. 2 | Alt. 1 | Alt. 2 |
| (42) circular | 9.5 | 9.5 | | | | |
| (43) Rectangular | | | (83) 5.0 | (83) 4.75 | 9.5 | 9.5 |
| (44) circular | 9.5 | 9.5 | | | | |
| (45) Rectangular | | | (84) 9.5 | (84) 9.5 | 5.0 | 4.25 |
| (46) circular | 9.5 | 9.5 | | | | |
| (47) Rectangular | | | (85) 5.0 | (85) 3.75 | 9.5 | 9.5 |
| (48) circular | 9.5 | 9.5 | | | | |
| (49) Rectangular | | | (86) 9.5 | (86) 9.5 | 5.0 | 3.5 |
| (50) circular | 9.5 | 9.5 | | | | |
| (51) circular | 6.0 | 6.0 | | | | |
| (52) circular | 6.0 | 6.0 | | | | |
| (53) Rectangular | | | (87) 3.5 | (87) 3.25 | 6.0 | 6.0 |
| (54) circular | 6.0 | 6.0 | | | | |
| (55) Rectangular | | | (88) 6.0 | (88) 6.0 | 3.5 | 3.25 |
| (56) circular | 6.0 | 6.0 | | | | |
| (57) Rectangular | | | (89) 3.5 | (89) 2.75 | 6.0 | 6.0 |
| (58) circular | 6.0 | 6.0 | | | | |
| (59) Rectangular | | | (90) 6.0 | (90) 6.0 | 3.5 | 2.75 |
| (60) circular | 6.0 | 6.0 | | | | |

TABLE 5

Examples of dimension parameters computed based on the desired mean rate of strain and/or based on a fixed length with hydraulic tube radius also applying to non-axisymmetric section of the disperser

| Tube diameter, $2R_0$ (mm) | Contraction diameter, $2R_1$ (mm) | Contraction ratio, CR as defined above | Volumetric flow rate (mm$^3$/s) | B; Fixed rate of strain (1/s) | Computed length, L (mm) for Fixed rate of strain equal to 10.0 (1/s) based on Eq. (1) | Computed Mean Rate of strain (1/s) based on Fixed Length of 10 mm based on Eq. (3) |
|---|---|---|---|---|---|---|
| 9.50 | 5.50 | 2.98 | 4000 | 10.00 | 11.2 | 11.19 |
| 9.50 | 4.50 | 4.46 | 4000 | 10.00 | 19.5 | 19.51 |
| 9.50 | 3.50 | 7.37 | 4000 | 10.00 | 35.9 | 35.93 |
| 6.00 | 3.50 | 2.94 | 4000 | 10.00 | 27.4 | 27.43 |
| 6.00 | 3.25 | 3.41 | 4000 | 10.00 | 34.1 | 34.07 |
| 6.00 | 2.75 | 4.76 | 4000 | 10.00 | 53.2 | 53.20 |

Example 2

Dispersion of Norway Spruce Somatic Embryos

One of the disperser systems built according to the invention consists of dimensions similar to the Table 3 Alt. 2 case with 6 ram-axisymmetric and 4 axi-symmetric sections positioned in series one after another in decreasing cross-sectional area of the constriction.

Several clusters of embryogenic mass of Norway Spruce (cell line 06:28:05) with average hydraulic diameter of the cross-section taken from the mid-section of the cluster ranging, from 5 nun to 30 mm were collected from a periodically and partially immersed bioreactor and fed into a disperser of the invention described above. A total of ten (10) take sections were attached by 180° circular tube bends in a spiral pattern. The lower section of the tube bends were fixed in plastic so the whole structure was permanently held in place. As the flow was initiated by a peristaltic pump, the clusters were observed entering the disperser and through the sections with axisymmetric and non-axisymmenic contraction and expansion sections. The embryos were observed to be completely dispersed as passing through the last section of the disperser, showing the effectiveness of the invention to fully disperse the cluster. The embryos were not physically damaged by the dispersion.

The invention claimed is:

1. A method of dispersion of clusters of plant embryos suspended in a liquid into individual plant embryos flowing through a flow channel, the method comprising:
feeding clusters of plant embryos into a disperser for separating individual plant embryos contained in the clusters of embryos;
subjecting the clusters of plant embryos to axially extensional strain and radially compressional strain;
subjecting the clusters of plant embryos to fluid dynamics forces causing axially compressional strain and radially extensional strain from fluid dynamics forces; and
repeating the subjecting steps in sequence until the individual plant embryos are separated from each other,
wherein the disperser comprises a flow channel including at least two constrictions,
wherein each constriction of the at least two constrictions has a cross-sectional area in the interval from 0.75 to 1300 mm2,
wherein the flow channel includes an intermediate portion between sequential constrictions,
wherein the minimum cross-sectional dimension of the flow channel is larger than the largest dimension of the largest part of an individual plant embryo in the clusters of plant embryos to be dispersed, and
wherein the longitudinal axes of said at least two constrictions align with each other.

2. The method of claim 1, wherein the strength of the extensional and compressional strains increases with each repeated sequence.

3. The method of claim 1, wherein each intermediate portion of the disperser, into which the clusters of plant embryos are fed, has a length at least equal to the largest dimension of any cluster of plant embryos to be dispersed.

4. The method of claim 3, wherein the length of each intermediate portion is in the interval from 2.5 mm to 60 mm.

5. The method of claim 1, wherein the disperser, into which the clusters of plant embryos are fed, comprises between 2 and 100 constrictions.

6. The method of claim 1, wherein each constriction of the plurality of constrictions of the disperser, into which the clusters of plant embryos are fed, has a cross-sectional area in the interval from 3 to 32 $mm^2$.

7. The method of claim 1, wherein the flow channel of the disperser, into which the clusters of plant embryos are fed, has an axisymmetric cross-section.

8. The method of claim 1, wherein the flow channel of the disperser, into which the clusters of plant embryos are fed, has an essentially circular or oval cross-section.

9. The method of claim 1, wherein at least part of the flow channel of the disperser, into which the clusters of plant embryos are fed, has a non-axisymmetric cross-section.

10. The method of claim 9, Wherein the cross-section of each non-axisymmetric constriction, having a maximal dimension, is oriented such that the maximal dimension of each constriction is rotated at least 30° in relation to the maximal dimension of the next non-axisymmetric constriction in sequence.

11. The method of claim 9, wherein the cross-section of each non-axisymmetric constriction is a rectangle, having a first and a second side, wherein the first side is longer than the second side, and the non-axisymmetric constrictions are oriented such that first side of each constriction is perpendicular to the first side of the next non-axisymmetric constriction in sequence having a rectangular cross-section.

12. The method of claim 4, wherein the length of each intermediate portion of the disperser, into which the clusters of plant embryos are fed, is in the interval from about 5 mm to about 30 mm.

13. The method of claim 5, wherein the disperser, into which the clusters of plant embryos are fed, comprises 5-20 constrictions.

14. The method of claim 5, wherein the disperser, into which the clusters of plant embryos are fed, comprises 10 constrictions.

15. The method of claim 10, wherein the maximal dimension of each constriction of the disperser, into which the clusters of plant embryos are fed, is rotated at least about 90° , in relation to the maximal dimension of the next non-axisymmetric constriction in sequence.

16. The method of claim 9, wherein each intermediate portion of the disperser, into which the clusters of plant embryos are fed, has an inner diameter that is equal to or smaller than the inner diameter of the intermediate portion immediately up-stream thereof.

17. The method of claim 1, wherein each constriction of the at least two constrictions has an inner diameter that is equal to or smaller than the inner diameter of the constriction immediately up-stream thereof.

18. The method of claim 1, wherein the intermediate portion has an essentially constant cross-section.

19. The method of claim 1, wherein each intermediate portion of the disperser, into which the clusters of plant embryos are fed, has an inner diameter that is equal to or smaller than the inner diameter of the intermediate portion immediately up-stream thereof.

20. The method of claim 7, wherein each intermediate portion of the disperser, into which the clusters of plant embryos are fed, has an inner diameter that is equal to or smaller than the inner diameter of the intermediate portion immediately up-stream thereof.

21. A method of dispersion of clusters of plant embryos suspended in a liquid into individual plant embryos flowing through a flow channel, the method comprising:

feeding clusters of plant embryos into a disperser for separating individual plant embryos contained in the clusters of embryos, subjecting the dusters of plant embryos to axially extensional strain and radially compressional strain;

subjecting the clusters of plant embryos to fluid dynamics forces causing axially compressional strain and radially extensional strain from fluid dynamics forces; and repeating the subjecting steps in sequence until the individual plant embryos are separated from each other, wherein the disperser comprises a flow channel including at least two constrictions, wherein each constriction of the at least two constrictions has an inner diameter that is equal to or smaller than the inner diameter of the constriction immediately up-stream thereof, wherein each constriction of the at least two constrictions has a cross-sectional area in the interval from 0.75 to 1300 $mm^2$, wherein the minimum cross-sectional dimension of the flow channel is larger than the largest dimension of the largest part of an individual plant embryos in the clusters of plant embryos to be dispersed, wherein the flow channel includes an intermediate portion between sequential constrictions, the intermediate portion having an essentially constant cross-section.

* * * * *